(12) United States Patent
Inoue

(10) Patent No.: US 8,430,822 B2
(45) Date of Patent: Apr. 30, 2013

(54) BLOOD PRESSURE MEASURING APPARATUS AND METHOD OF CONTROLLING THE SAME

(75) Inventor: Kouichi Inoue, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 221 days.

(21) Appl. No.: 12/854,345

(22) Filed: Aug. 11, 2010

(65) Prior Publication Data

US 2010/0324430 A1 Dec. 23, 2010

Related U.S. Application Data

(63) Continuation of application No. PCT/JP2009/050739, filed on Jan. 20, 2009.

(30) Foreign Application Priority Data

Feb. 12, 2008 (JP) .................................. 2008-030717

(51) Int. Cl.
*A61B 5/02* (2006.01)
(52) U.S. Cl.
USPC .......................... 600/499; 600/490; 600/492
(58) Field of Classification Search .......... 600/485–499
See application file for complete search history.

(56) References Cited

U.S. PATENT DOCUMENTS

| | | | |
|---|---|---|---|
| 8,100,835 B2 * | 1/2012 | Baruch ......................... | 600/485 |
| 2004/0181254 A1 | 9/2004 | Choi et al. | |
| 2007/0010749 A1 * | 1/2007 | Meng ........................... | 600/490 |

FOREIGN PATENT DOCUMENTS

| | | |
|---|---|---|
| JP | 2003-093357 A | 4/2003 |
| JP | 2005-185295 A | 7/2005 |
| JP | 2007-125247 A | 5/2007 |
| JP | 2008-005926 A | 1/2008 |
| JP | 2008-005927 A | 1/2008 |

OTHER PUBLICATIONS

EPO provided translation of Written Opinion (PCT/ISA/237) issued on Feb. 17, 2009, by Japanese Patent Office as the International Searching Authority for International Application No. PCT/JP2009/050739.*
International Search Report (PCT/ISA/210) issued on Feb. 17, 2009, by Japanese Patent Office as the International Searching Authority for International Application No. PCT/JP2009/050739.
Written Opinion (PCT/ISA/237) issued on Feb. 17, 2009, by Japanese Patent Office as the International Searching Authority for International Application No. PCT/JP2009/050739.

* cited by examiner

*Primary Examiner* — Patricia Mallari
*Assistant Examiner* — Mitchell Alter
(74) *Attorney, Agent, or Firm* — Buchanan Ingersoll & Rooney PC

(57) ABSTRACT

A high-accuracy blood pressure value deriving method that is hardly influenced by individual differences of a person to be measured is provided. A blood pressure measuring apparatus includes a cuff member comprising a compression air bladder, a sub air bladder, and a pulse wave detection air bladder, pressure control means for pressurizing or depressurizing each air bladder, a pressure sensor which senses the internal pressure of each air bladder, pulse wave signal extracting means for extracting time-series data of a pulse wave signal superposed on a cuff internal pressure, in the process during which the pressure control means pressurizes or depressurizes each air bladder, and blood pressure value deriving means for deriving a systolic blood pressure value and/or a diastolic blood pressure value based on a change in feature amount of the pulse wave signal and a cuff internal pressure at a point of time of the change.

4 Claims, 11 Drawing Sheets

ONE-PERIOD PULSE WAVE IN CUFF PRESSURE HIGHER THAN DIASTOLIC BLOOD PRESSURE VALUE

ONE-PERIOD PULSE WAVE IN DIASTOLIC BLOOD PRESSURE

BLOOD PRESSURE MEASURING APPARATUS AND METHOD OF CONTROLLING THE SAME

TECHNICAL FIELD

The present invention relates to a technique to measure the blood pressure based on the change in a pulse wave detected when the cuff pressure of a cuff attached to a measurement portion is changed and, more particularly, to a technique of determining a diastolic blood pressure value and systolic blood pressure value.

BACKGROUND ART

Measuring blood pressure is very important in antihypertensive therapy. According to the guidelines for antihypertensive therapies of WHO/ISH, the degrees of hypertension are classified in accordance with blood pressure values measured every 5 mmHg, and therapeutic methods suitable for the individual degrees are recommended. Therefore, whether appropriate therapies can be performed depends on the measured blood pressure values. Also, as the aging population advances, demands for high accuracy and high reliability of blood pressure measurement are on the rise in order to prevent circulatory organ diseases and metabolic syndrome of which hypertension has a large effect on.

Conventionally, as measurement methods of a non-invasive sphygmomanometer for measuring the blood pressure by winding a cuff around a blood pressure measurement portion, and gradually changing the cuff pressure from a pressure higher than the systolic blood pressure (also called a maximum blood pressure) to a pressure lower than the diastolic blood pressure (also called a minimum blood pressure), the microphone method that measures the blood pressure by detecting the Korotkoff sounds as in the auscultatory method and the oscillometric method that measures the blood pressure by detecting the change in pulse wave superposed on the internal pressure of an internal air bladder of a cuff are used.

In the oscillometric method, for example, when the cuff pressure is gradually changed from a pressure (for example, 180 mmHg) equal to or higher than the systolic blood pressure value to a pressure (for example, 60 mmHg) equal to or lower than the diastolic blood pressure value, the amplitude of a detected pulse wave initially shows an almost constant value but gradually increases as the cuff pressure approaches the systolic blood pressure value. When the cuff pressure becomes equal to or lower than the systolic blood pressure and approaches the diastolic blood pressure, the amplitude of the pulse wave reaches its maximum and then gradually decreases. Furthermore, when the cuff pressure becomes equal to or lower than the diastolic blood pressure value, the amplitude of the pulse wave gradually changes to approach a certain predetermined value. In the oscillometric method, therefore, a time-series pulse wave amplitude change profile corresponding to the change in cuff pressure is normalized as is indicated by the ratio (%) of each pulse wave amplitude based on a maximum pulse wave amplitude of the magnitude of a detected pulse wave. At the same time, the ratio of a pulse wave corresponding to the systolic blood pressure value and diastolic blood pressure value measured by the auscultatory method (K method) is obtained from the average value of many actual data. This value is 50% for the systolic blood pressure, and 60% to 80% for the diastolic blood pressure.

Unfortunately, the relationship between the blood pressure value obtained by the auscultatory method and the ratio of the pulse wave amplitude described above is influenced by individual differences in blood pressure value, pulse strength, and shape of the invasive blood pressure waveform as the blood vessel internal pressure. This relationship is also influenced by the factors of measurement methods, for example, the variation in cuff-edge effect (a phenomenon in which the blood vessel pressing force in the end portions of a cuff is weaker than that in the central portion) in the upstream and downstream portions of a cuff, which is caused by the way the cuff is wound, and the change in compliance (the change in pulse wave detection sensitivity) caused by the way the cuff is wound. A cardiac output phenomenon in a cuff peripheral portion is influenced by individual differences in blood vessel elasticity and blood vessel volume in the forearm and hand as peripheral portions of a cuff attachment portion, the individual differences in degree of the peripheral circulation of the blood after the blood pressure is measured, and the rise in peripheral blood vessel internal pressure due to the degree of congestion of the blood vessel on the cuff peripheral side, which is affected by the shortness of the repetition time of blood pressure measurement.

Most of the influencing factors are problems caused by individual differences, and difficult to directly control. Controlling the way a cuff is wound has a large effect on the usability of blood pressure measurement. Therefore, as a method of reducing the influencing factors in the measurement of the systolic blood pressure, the S/N ratio is increased by raising the sensitivity of detection of a pulse wave output to the cuff peripheral side. For example, patent reference 1 has proposed a double-cuff method that improves the ability to detect a pulse wave output to the cuff peripheral side, which is the key point of systolic blood pressure measurement, by installing a pulse wave detection air bladder for selectively detecting the cardiac output on the cuff peripheral side, in a cuff central portion where the pressure of a compression air bladder is most reflected.

PLT1: Japanese Patent Laid-Open No. 2005-185295

DISCLOSURE OF INVENTION

Problem to be Solved by Invention

Even when using the so-called double-cuff method described above, however, it is sometimes impossible to ensure a high S/N ratio owing to the cuff-edge effect that prevents the detection of a pulse wave signal by the cardiac output on the cuff peripheral side when the cuff pressure is higher than the systolic blood pressure, and a cuff upstream pulse wave generated in a cuff upstream portion by the change in blood flow that enters and is pushed back in synchronism with contraction and relaxation of the heart. Also, even when using the double-cuff method, it is sometimes necessary to use a method complying with the oscillometric method that derives a blood pressure value by the correlation with the diastolic blood pressure of the auscultatory method when a pulse wave is small. In this case, the double-cuff method is influenced by individual differences. To perform more accurate measurement, therefore, it is necessary to perform blood pressure measurement a plurality of number of times, or perform measurement by a doctor by using the auscultatory method.

The present invention has been made in consideration of the above-described problems, and has as its object to provide a high-accuracy blood pressure value deriving method that is hardly influenced by individual differences of a person to be measured.

Means for Solving Problem

To solve the above-described problems, a blood pressure measuring apparatus of the present invention has the following arrangement. That is, a blood pressure measuring apparatus is characterized by comprising a cuff member comprising a compression air bladder which is formed on a side to be brought into contact with a blood pressure measurement portion and presses a whole blood pressure measurement portion, a sub air bladder which is formed on a side of the compression air bladder, which is brought into contact with the blood pressure measurement portion, and presses a heart side of a blood vessel in the blood pressure measurement portion, and a pulse wave detection air bladder which is formed on the side of the compression air bladder, which is brought into contact with the blood pressure measurement portion, and detects a pulse wave on a slightly downstream side of a central portion of the blood vessel in the blood pressure measurement portion, pressure control means for pressurizing or depressurizing each air bladder of the cuff member, a pressure sensor which senses an internal pressure of each air bladder of the cuff member, pulse wave signal extracting means for extracting time-series data of a pulse wave signal superposed on a cuff internal pressure sensed by the pressure sensor, in the process during which the pressure control means pressurizes or depressurizes each air bladder of the cuff member, and blood pressure value deriving means for deriving a systolic blood pressure value and/or a diastolic blood pressure value based on a change in feature amount of the pulse wave signal and a cuff internal pressure at a point of time of the change, wherein the blood pressure value deriving means detects, for each of a plurality of one-period pulse wave signals contained in the pulse wave signal time-series data, a maximum gradient point of the one-period pulse wave in a period between a peak point and a bottom point appearing prior to the peak point, and derives the systolic blood pressure value and/or the diastolic blood pressure value based on a difference between a pulse wave amplitude value at a bottom point appearing prior to the detected maximum gradient point and a value, which is obtained at a time of the bottom point, of a tangent passing through the detected maximum gradient point.

Also, a blood pressure measuring apparatus is characterized by comprising a cuff member comprising a compression air bladder which is formed on a side to be brought into contact with a blood pressure measurement portion and presses a whole blood pressure measurement portion, a sub air bladder which is formed on a side of the compression air bladder, which is brought into contact with the blood pressure measurement portion, and presses a heart side of a blood vessel in the blood pressure measurement portion, and a pulse wave detection air bladder which is formed on the side of the compression air bladder, which is brought into contact with the blood pressure measurement portion, and detects a pulse wave on a slightly downstream side of a central portion of the blood vessel in the blood pressure measurement portion, pressure control means for pressurizing or depressurizing each air bladder of the cuff member, a pressure sensor which senses an internal pressure of each air bladder of the cuff member, pulse wave signal extracting means for extracting time-series data of a pulse wave signal superposed on a cuff internal pressure sensed by the pressure sensor, in the process during which the pressure control means pressurizes or depressurizes each air bladder of the cuff member, and blood pressure value deriving means for deriving a systolic blood pressure value and/or a diastolic blood pressure value based on a change in feature amount of the pulse wave signal and a cuff internal pressure at a point of time of the change, wherein the blood pressure value deriving means detects, for each of a plurality of one-period pulse wave signals contained in the pulse wave signal time-series data, a maximum gradient point of the one-period pulse wave in a period between a peak point and a bottom point appearing prior to the peak point, and derives the systolic blood pressure value and/or the diastolic blood pressure value based on an area of a portion bounded by a tangent passing through the detected maximum gradient point and the pulse wave signal in a period between the maximum gradient point and a bottom point appearing prior to the maximum gradient point.

To solve the above-described problems, a method of controlling a blood pressure measuring apparatus of the present invention has the following arrangement. That is, a method of controlling a blood pressure measuring apparatus comprising a cuff member comprising a compression air bladder which is formed on a side to be brought into contact with a blood pressure measurement portion and presses a whole blood pressure measurement portion, a sub air bladder which is formed on a side of the compression air bladder, which is brought into contact with the blood pressure measurement portion, and presses a heart side of a blood vessel in the blood pressure measurement portion, and a pulse wave detection air bladder which is formed on the side of the compression air bladder, which is brought into contact with the blood pressure measurement portion, and detects a pulse wave on a slightly downstream side of a central portion of the blood vessel in the blood pressure measurement portion, pressure control means for pressurizing or depressurizing each air bladder of the cuff member, and a pressure sensor which senses an internal pressure of each air bladder of the cuff member, is characterized by comprising a pulse wave signal extracting step of extracting time-series data of a pulse wave signal superposed on a cuff internal pressure sensed by the pressure sensor, in the process during which the pressure control means pressurizes or depressurizes each air bladder of the cuff member, and a blood pressure value deriving step of deriving a systolic blood pressure value and/or a diastolic blood pressure value based on a change in feature amount of the pulse wave signal and a cuff internal pressure at a point of time of the change, wherein in the blood pressure value deriving step, for each of a plurality of one-period pulse wave signals contained in the pulse wave signal time-series data, a maximum gradient point of the one-period pulse wave is detected in a period between a peak point and a bottom point appearing prior to the peak point, and the systolic blood pressure value and/or the diastolic blood pressure value is derived based on a difference between a pulse wave amplitude value at a bottom point appearing prior to the detected maximum gradient point and a value, which is obtained at a time of the bottom point, of a tangent passing through the detected maximum gradient point.

Also, a method of controlling a blood pressure measuring apparatus comprising a cuff member comprising a compression air bladder which is formed on a side to be brought into contact with a blood pressure measurement portion and presses a whole blood pressure measurement portion, a sub air bladder which is formed on a side of the compression air bladder, which is brought into contact with the blood pressure measurement portion, and presses a heart side of a blood vessel in the blood pressure measurement portion, and a pulse wave detection air bladder which is formed on the side of the compression air bladder, which is brought into contact with the blood pressure measurement portion, and detects a pulse wave on a slightly downstream side of a central portion of the blood vessel in the blood pressure measurement portion, pressure control means for pressurizing or depressurizing each air bladder of the cuff member, and a pressure sensor which senses an internal pressure of each air bladder of the cuff member, is characterized by comprising a pulse wave signal extracting step of extracting time-series data of a pulse wave signal superposed on a cuff internal pressure sensed by the pressure sensor, in the process during which the pressure control means pressurizes or depressurizes each air bladder of the cuff member, and a blood pressure value deriving step of deriving a systolic blood pressure value and/or a diastolic blood pressure value based on a change in feature amount of the pulse wave signal and a cuff internal pressure at a point of time of the change, wherein in the blood pressure value deriving step, for each of a plurality of one-period pulse wave signals contained in the pulse wave signal time-series data, a maximum gradient point of the one-period pulse wave is detected in a period between a peak point and a bottom point appearing prior to the peak point, and the systolic blood pressure value and/or the diastolic blood pressure value is derived based on an area of a portion bounded by a tangent passing through the detected maximum gradient point and the pulse wave signal in a period between the maximum gradient point and a bottom point appearing prior to the maximum gradient point.

Effects of Invention

The present invention can provide a blood pressure measuring apparatus having a high-accuracy blood pressure value deriving method that is hardly influenced by individual differences of a person to be measured, and a method of controlling the same.

Other features of the present invention will be apparent from the following best mode for carrying out the invention and the accompanying drawings. Note that the same reference numerals denote the same or similar parts in the accompanying drawings.

BRIEF DESCRIPTION OF DRAWINGS

The accompanying drawings, which are incorporated in and constitute a part of the specification, illustrate an embodiment of the invention and, together with the description, serve to explain the principle of the invention.

BEST MODE FOR CARRYING OUT INVENTION

First Embodiment

A preferred embodiment of a blood pressure measuring apparatus of the present invention will be explained below with reference to the accompanying drawings. Note that this embodiment will be explained by taking, as an example, a blood pressure measuring apparatus including a compression air bladder, pulse wave detection air bladder, and sub air bladder (a so-called triple cuff). Note also that in the following description, a pulse wave signal obtained when using the triple cuff of the present invention in a cuff depressurizing process will be explained in detail, and then details of the operation of the blood pressure measuring apparatus of the present invention will be explained.

Apparatus Configuration

Figure 11:
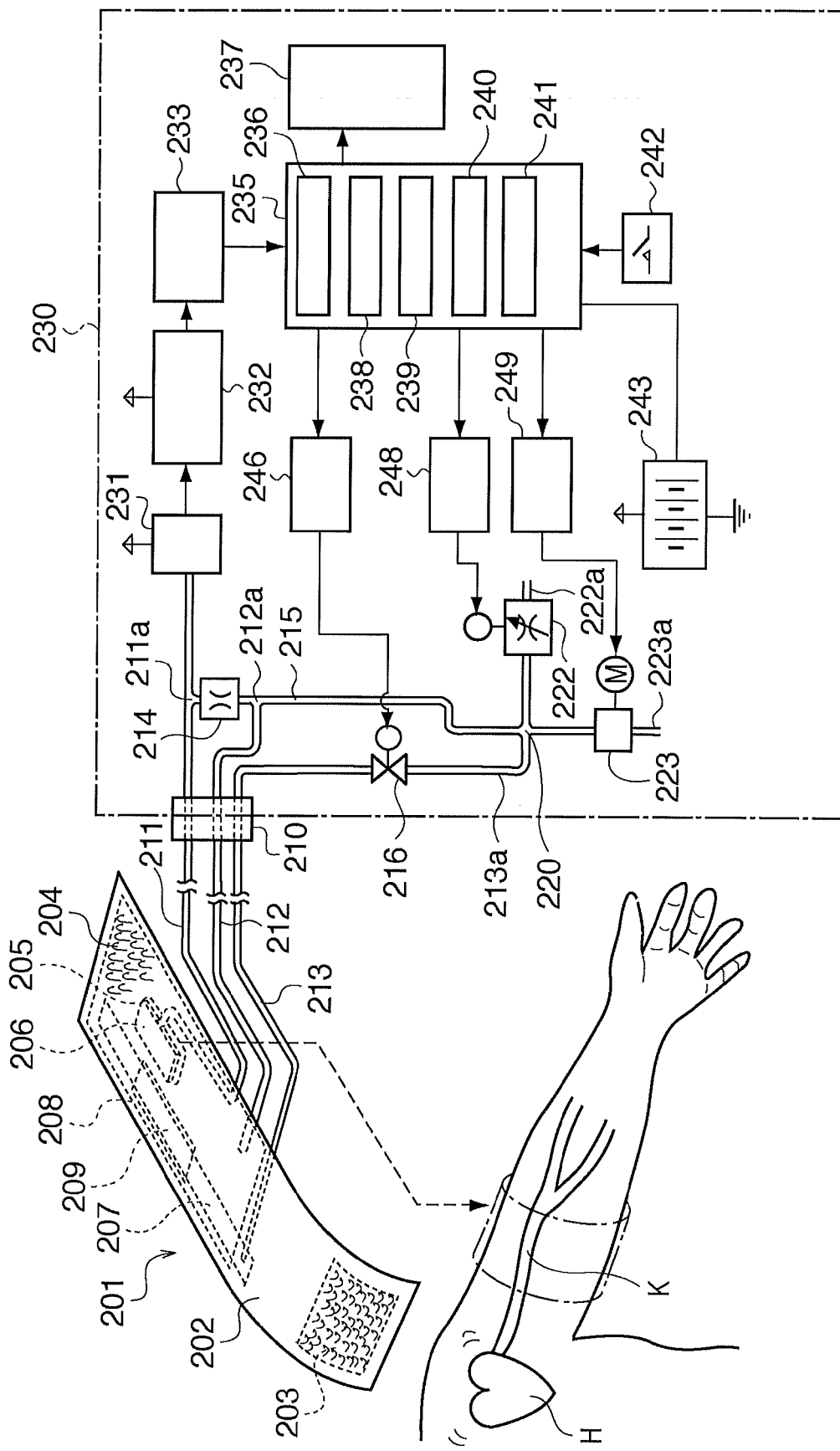
FIG. 11 is a view that depicts the arrangement of the blood pressure measuring apparatus according to the first embodiment.

FIG. 11 is a block diagram that depicts a blood pressure measuring apparatus according to the first embodiment. A cuff main body 201 includes a cloth cuff member 202 that can be attached to and detached from a blood pressure measurement portion including the upper arm. The end portion of the side of the cuff member 202, which is brought into contact with the measurement portion has a male (hook) hook-and-loop fastener 203 indicated by broken lines. The surface opposite to the side to be brought into contact with the measurement portion has a female (loop) hook-and-loop fastener 204 having the same position and area as those of a compression air bladder. The cuff main body 201 can be attached by winding the cuff member 202 around the upper arm as shown in FIG. 11, and locking the hook-and-loop fasteners. Note that the hook-and-loop fasteners are merely examples, and other members may be used. It is also possible to use a cylindrical cuff member into which the upper arm is inserted.

A compression air bladder 208 indicated by broken lines is formed inside the cuff member 202, in order to press a whole blood pressure measurement portion. A sub air bladder 207 indicated by broken lines is formed on the side of the compression air bladder 208, which is brought into contact with the blood pressure measurement portion. The sub air bladder 207 has a small width in order to press the side of the blood pressure measurement portion, which is close to a heart H. A first damping member 209 is formed between the sub air bladder 207 and compression air bladder 208 so as to cover the whole sub air bladder 207, and damps the vibration of the sub air bladder 207.

Also, a pulse wave detection air bladder 205 indicated by broken lines is formed on the side of the compression air bladder 208, which is brought into contact with the blood pressure measurement portion. The pulse wave detection air bladder 205 presses the blood vessel downstream side of the blood pressure measurement portion, and detects a pulse wave on the downstream side. The cuff main body 201 is constructed as above.

To pressurize and depressurize the cuff main body 201, a pump 223 as a pressurizing/depressurizing means is connected to the compression air bladder 208 of the cuff main body 201 via a second tube 212 and tube 215, to the pulse wave detection air bladder 205 of the cuff main body 201 via a first tube 211 and fluid resistor 214, and to the sub air bladder 207 of the cuff main body 201 via a third tube 213 and opening/closing valve 216. Also, a pressure sensor 231 as a cuff pressure detecting means for obtaining a cuff pressure signal from the change in pressure of the pulse wave detection air bladder 205 is connected to the pulse wave detection air bladder 205 via the first tube 211. Furthermore, the third tube 213 is connected to the sub air bladder 207.

The first, second, and third tubes 211, 212, and 213 are made of soft tubes, and attachable to and detachable from a main body 230 via a connector 210. The third tube 213 is preferably further connected to a damper device 218 (indicated by broken lines) that increases the volume in proportion to the pressure and smoothes the pressure.

A cross branched portion 220 is connected to the pump 223 and a rapid exhaust valve/constant-rate exhaust valve 222. The rapid exhaust valve/constant-rate exhaust valve 222 is connected to a controller 248, and the opening/closing valve 216 is connected to a controller 246. The opening area of a solenoid valve of the rapid exhaust valve/constant-rate exhaust valve 222 and the opening/closing operation of a solenoid opening/closing valve of the opening/closing valve 216 are controlled in accordance with commands from a central controller 235.

The pump 223 is driven by power supply from a pump driver 249 connected to a motor M, and supplies the external air into the pump through an opening 223a, thereby performing pressurization. That is, the air bladders can be pressurized by supplying the pressurizing air to the tube 215 and a third tube portion 213a via the cross branched portion 220.

The rapid exhaust valve/constant-rate exhaust valve 222 has a structure in which the opening area can be changed by the magnitude of the electromagnetic force in order to achieve a depressurization rate of 2 to 4 mmHg/sec. An arbitrary depressurization rate can be set by obtaining a PWM driving signal from the controller 248.

The pressure sensor 231 as a cuff pressure detecting means receives a compression pressure signal from the compression air bladder 208, in which the pulse wave component is attenuated via the fluid resistor 214, and the pressure change of the pulse wave detection air bladder 205. A pressure measuring unit 232 for conversion into an analog electrical signal is connected to the pressure sensor 231, and an A/D converter 233 is connected to the pressure measuring unit 232. The A/D converter 233 outputs a digital signal as a cuff pressure signal to the central controller 235.

The central controller 235 includes a RAM 238 for performing, for example, read and write of measurement data and analytical results, and a ROM 236 storing, as various control programs readable by the central controller 235, a pulse wave processor 239 for detecting a pulse wave signal superposed on a cuff pressure signal, a cuff pressure controller 240 for pressurizing and depressurizing the cuff (the compression air bladder, pulse wave detection air bladder, and sub air bladder), a blood pressure measuring unit 241 for determining the blood pressure from the detected pulse wave change and compression cuff pressure signal, and a display controller 237a for displaying the measured blood pressure value on a blood pressure display means 237. Note that the RAM 238 also functions as a work area of programs to be processed by the central controller 235.

The central controller 235 is also connected to the liquid crystal display 237 as a blood pressure display means for displaying the blood pressure value, and to drivers for performing the above-mentioned driving control operations.

Also, power supply from a power supply unit 243 including batteries is performed such that the central controller 235 can perform each operation required for blood pressure measurement by supplying power to the corresponding unit in accordance with the operation of a switch 242.

The blood pressure measuring apparatus configured as described above can be operated as shown in flowcharts of blood pressure measuring routines (to be described later) by the central controller 235 by reading out the various measurement control programs prestored in the ROM 236.

Cuff Pressing Force and Pulse Wave Signal

Figure 1:
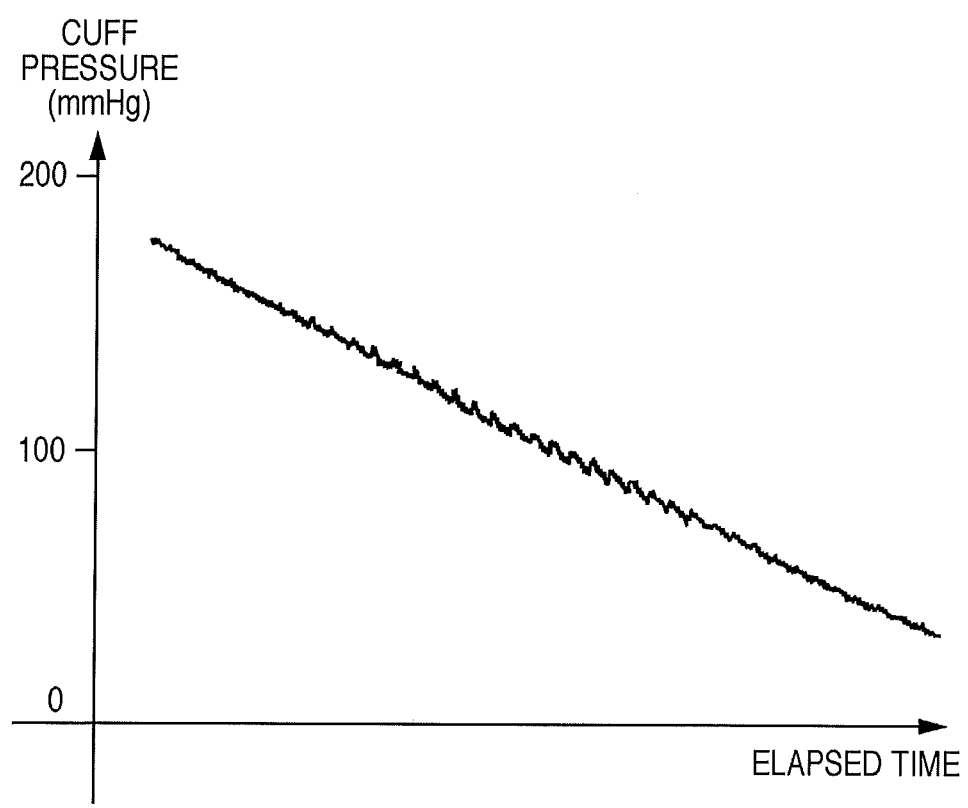
FIG. 1 is a view that depicts the way a pulse wave signal is superposed on the cuff pressure in a cuff depressurizing process.
Figure 2:
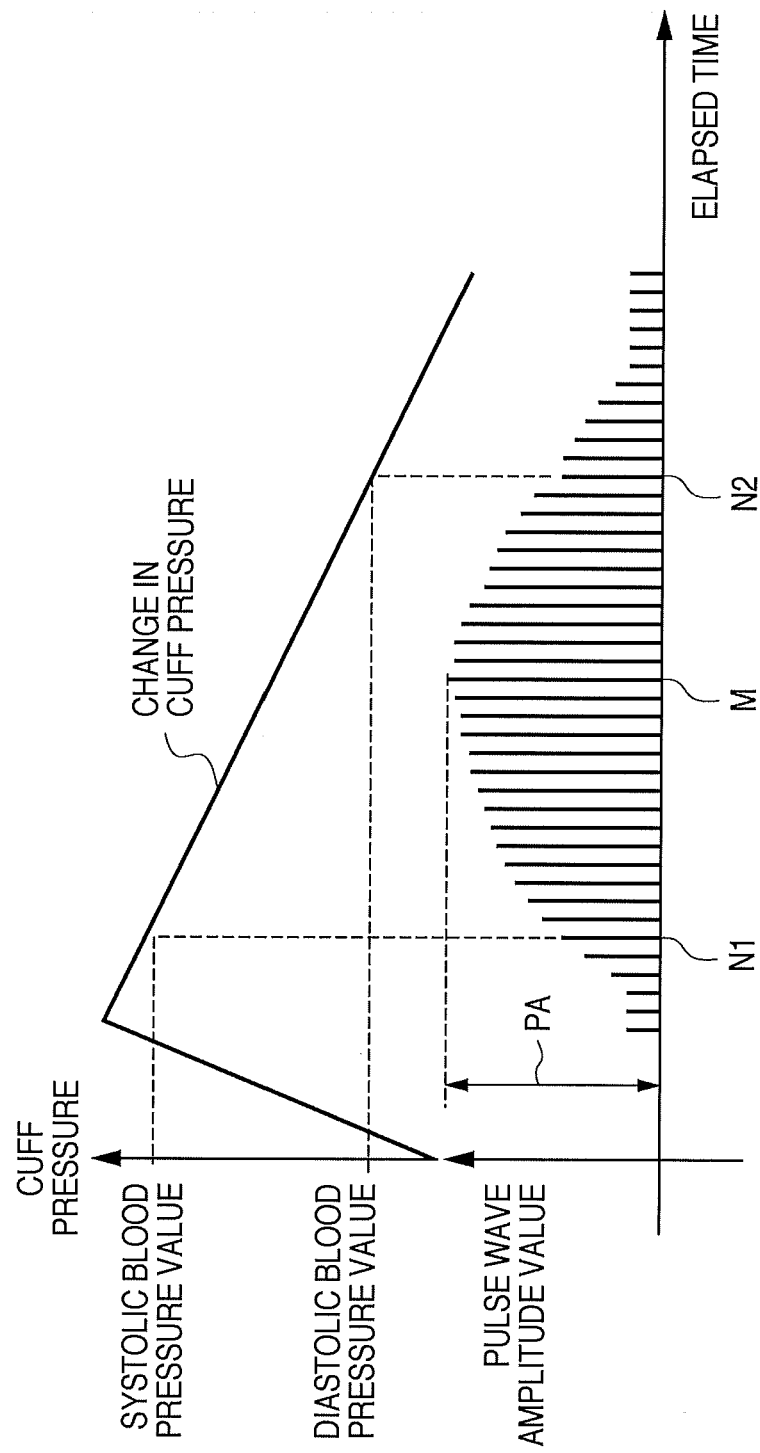
FIG. 2 is a view that depicts the way a pulse wave amplitude value to be superposed on the cuff pressure changes in the cuff depressurizing process, together with the change in cuff pressure.

FIG. 1 is a graph that depicts the way a pulse wave signal is superposed on the cuff pressure in a cuff depressurizing process. This graph shows the way the magnitude and shape of the pulse wave signal change as the cuff pressure reduces. FIG. 2 is a view that depicts the way a pulse wave amplitude value superposed on the cuff pressure changes in the cuff depressurizing process, together with the change in cuff pressure. FIG. 2 shows that in the cuff depressurizing process, the pulse wave amplitude value gradually increases and then gradually decreases after a point M at which a maximum amplitude value appears.

Figure 3:
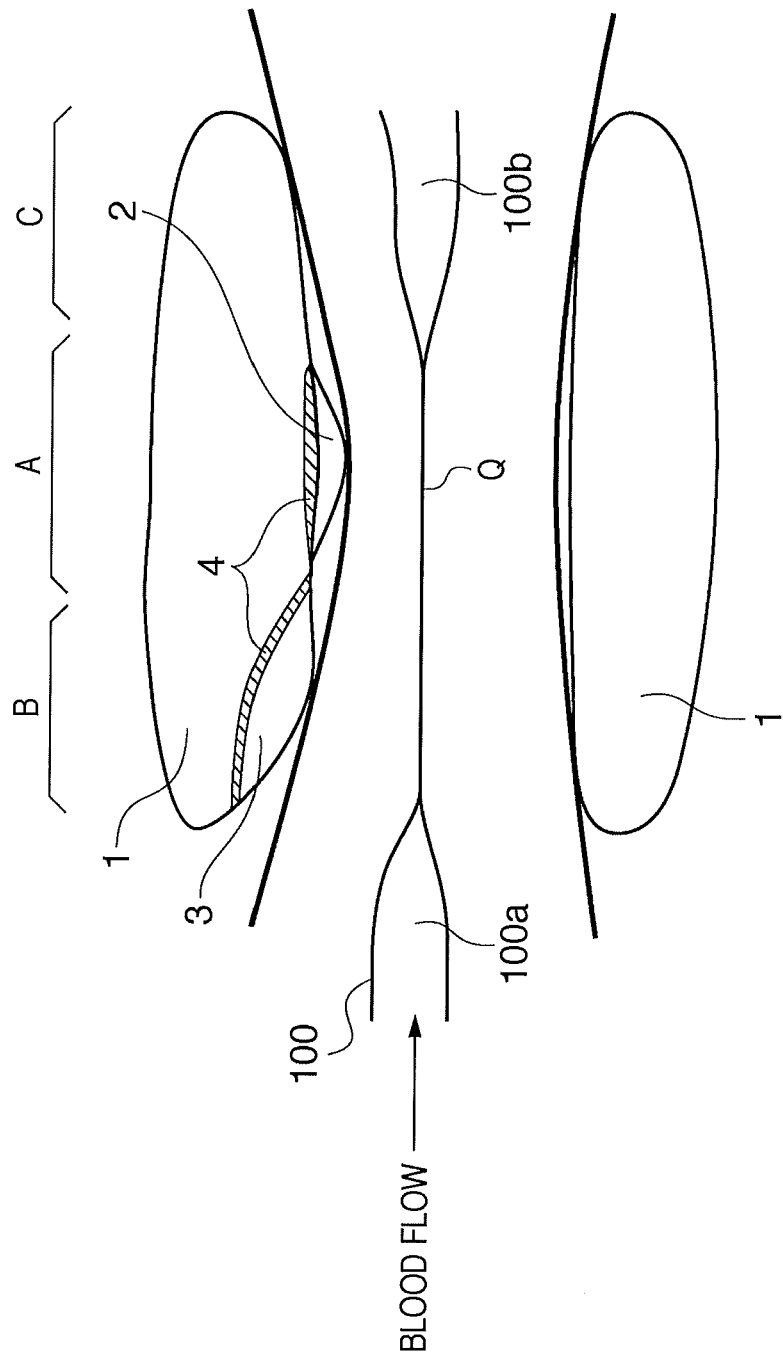
FIG. 3 is a sectional view in the longitudinal direction of a cuff of a blood pressure measuring apparatus according to the first embodiment.

FIG. 3 is a sectional view in the longitudinal direction (the direction in which the upper arm extends) of the cuff (triple cuff) of the blood pressure measuring apparatus according to the first embodiment. The cuff according to the first embodiment is a triple cuff including a large cuff 1 for occluding a blood vessel, a small cuff 2 for detecting a pulse wave, and a sub cuff 3 formed in an upstream portion. FIG. 3 shows the way the pressurized large cuff 1 for occluding a blood vessel and the pressurized sub cuff 3 occlude a portion Q of a blood vessel 100, thereby suppressing a blood flow from an upstream side 100a to a downstream side 100b.

The force with which the large cuff 1 presses the arm is strongest in a central portion (a portion A in FIG. 3; to be simply referred to as a cuff central portion A hereinafter) in the cuff widthwise direction. The pressing force weakens toward the two ends, and becomes almost 0 at the two ends. Note that this triple cuff differs from a double cuff including no sub cuff 3 in that the effect of the sub cuff 3 inhibits the blood flow from entering a section indicated by "B" in FIG. 3. The small cuff 2 is formed in the cuff central portion A in the cuff widthwise direction, and hence best detects a blood vessel internal pressure change (blood vessel internal volume change) in this portion. Note that "the cuff pressure" means the internal pressure of the cuff in this specification. In practice, however, the cuff pressure is equal to the arm pressing force in the cuff central portion A in the cuff widthwise direction. Therefore, the cuff pressure is also the pressure applied from the cuff to the blood vessel below the cuff central portion A in the cuff widthwise direction.

Properties of Components Forming Pulse Wave Signal

A pulse wave signal to be superposed on the cuff pressure, which is detected by the small cuff 2 for detecting a pulse wave, is mainly divided into a component W1 (to be referred to as a W1 component hereinafter) resulting from a direct cuff internal pressure change corresponding to a blood vessel internal volume change caused by a blood flow output from the upstream side of the cuff, and a component W2 (to be referred to as a W2 component hereinafter) resulting from a cuff internal pressure change corresponding to a blood vessel internal volume change caused by the reflection from a blood vessel on the downstream side of the cuff. The W1 component can be divided into a component W1-A (to be referred to as a W1-A component hereinafter) resulting from a pressure change (blood vessel internal volume change) below the central portion in the cuff widthwise direction, that is, the cuff central portion A, a component W1-B (to be referred to as a W1-B component hereinafter) resulting from a pressure change (blood vessel internal volume change) below an upstream portion in the cuff widthwise direction, that is, a portion B (to be simply referred to as a cuff upstream portion B hereinafter) shown in FIG. 3, and a component W1-C (to be referred to as a W1-C component hereinafter) resulting from a blood vessel internal volume change below a downstream portion in the cuff widthwise direction, that is, a portion C (to be simply referred to as a cuff downstream portion C hereinafter) shown in FIG. 3. In addition, the pulse wave signal contains, albeit slightly, a component W0 resulting from the vibration of a blood vessel caused by the blood vessel internal pressure.

Figure 4:
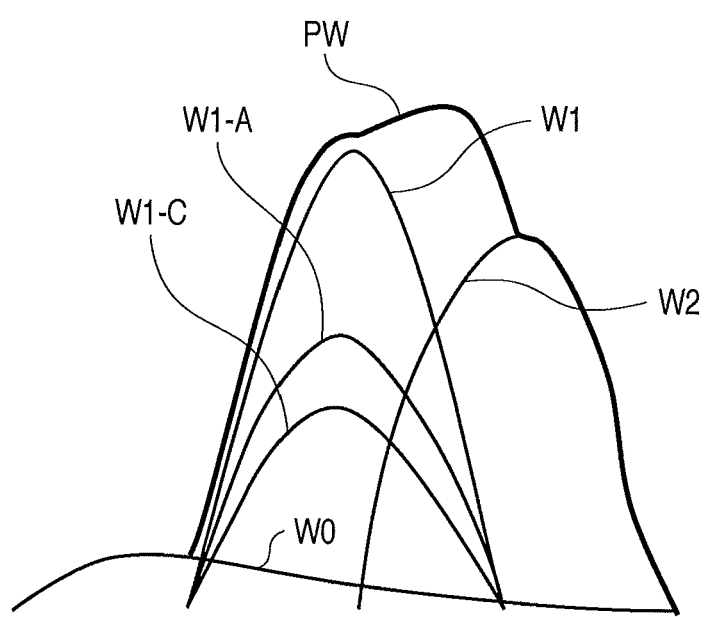
FIG. 4 is an exemplary view that depicts each component contained in a pulse wave signal PW.

FIG. 4 is an exemplary view that depicts the components contained in a pulse wave signal PW acquired by the triple-cuff method. More specifically, the pulse wave signal PW indicated by the thick line contains the W1 and W2 components, and the W1 component further contains the W1-A and W1-C components. Note that when compared to a double cuff including no sub cuff 3, the sub cuff 3 compensates for the cuff-edge effect of the large cuff 1, thereby largely reducing the W1-B component resulting from the blood vessel internal volume change caused by the blood flowing below the cuff upstream portion B.

Note that the W0 component as the vibration component of the blood vessel produced by the blood vessel internal pressure can newly be observed, because the W1-B component is suppressed. However, the amplitude change of the W0 component is much smaller than those of the W1-A and W1-C components.

The pulse wave signal PW is a typical example observed when the cuff pressure is between the systolic blood pressure value and diastolic blood pressure value in the depressurizing process. When the cuff pressure is between the systolic blood pressure value and diastolic blood pressure value in the depressurizing process, a phenomenon in which the blood flows into the cuff central portion A and outputs a blood flow to the blood vessel on the downstream side of the cuff is observed. In this case, the W1-A component resulting from the blood vessel internal volume change below the cuff central portion A caused by the blood flow output to the blood vessel on the downstream side and the W1-C component resulting from the blood vessel internal volume change below the cuff downstream portion C overlap each other to form the W1 component. In addition, the W2 component due to the reflection from the downstream side overlaps the W1 component with a time difference, thereby forming the pulse wave signal PW superposed on the cuff pressure.

The small cuff 2 for detecting a pulse wave is attached to the cuff central portion A, and hence best detects the W1-A component compared to the W0 and W1-C components. Accordingly, the feature of the W1-A component is largely reflected on the shape of the W1 component, compared to the feature of the W1-C component.

The W1-C component indicates the blood vessel internal volume change below the cuff downstream portion C. Since the downstream portion C is positioned downstream of the central portion A and the cuff pressing force in the downstream portion C is smaller than that in the central portion A, the opening/closing of the blood vessel below the downstream portion C is almost synchronized with that of the blood vessel below the central portion A, and there is practically no time difference between the appearances of the W1-A and W1-C components.

The W2 component is the reflection from the blood vessel on the downstream side of the cuff with respect to the blood flow output from the upstream side. Therefore, the peak appears later than that of the W1 component in accordance with the timing at which the blood vessel internal pressure on the downstream side becomes higher than the cuff pressure (FIG. 4). The reflection of the shape of the W2 component on the overall shape of the pulse wave signal is generally smaller than that of the shape of the W1 component (the synthesis of the W1-A and W1-C components). Also, when the cuff pressure is close to the diastolic blood pressure value in the depressurizing process, the blood vessel internal pressure on the cuff downstream side has sufficiently recovered to the state before the blood flow is occluded by the cuff, so there is practically no reflection from the blood vessel on the downstream side. Accordingly, the W2 component has practically disappeared from a pulse wave signal detected when the cuff pressure is close to the diastolic blood pressure value.

Figure 5:
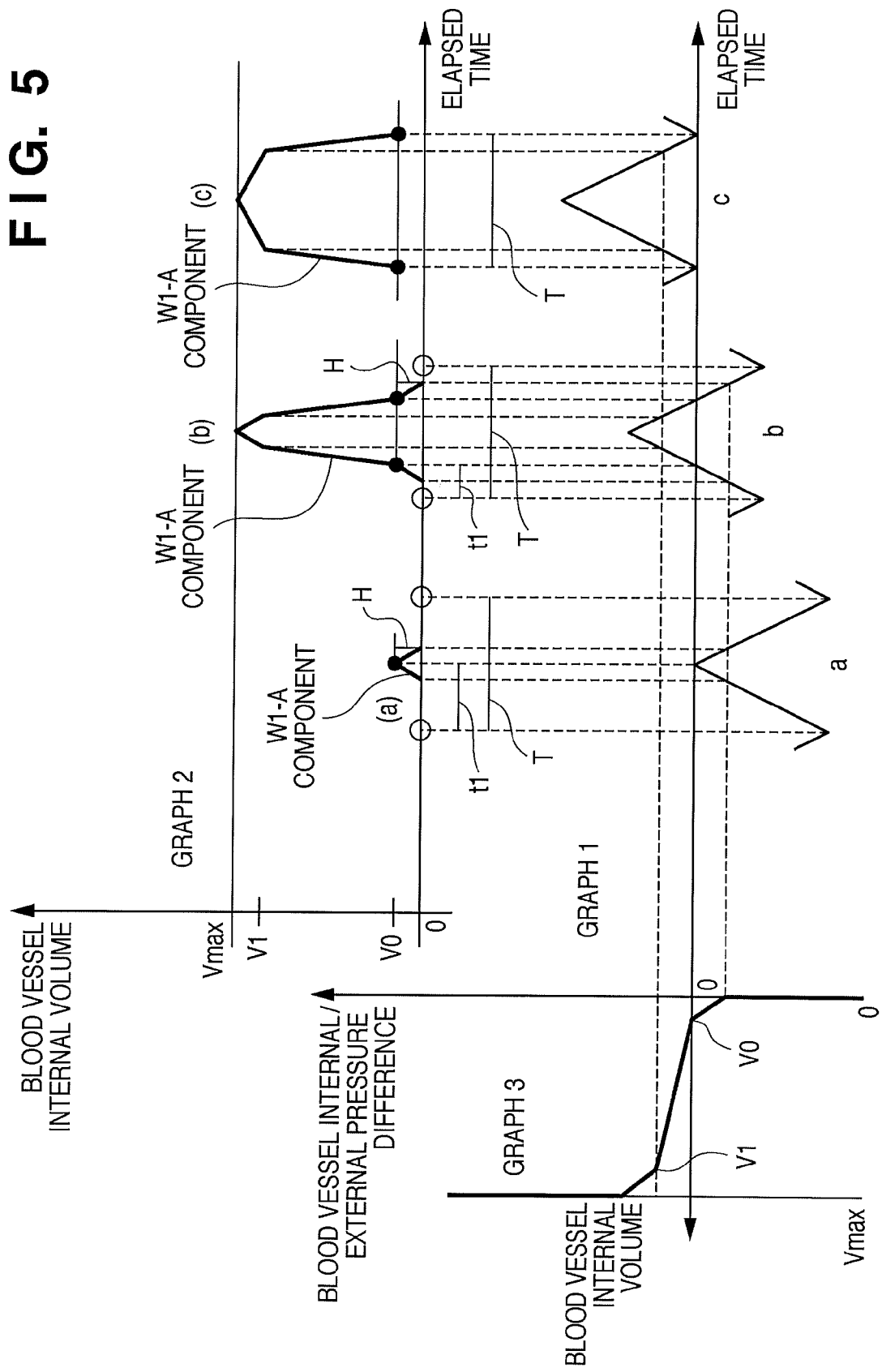
FIG. 5 is an exemplary view that depicts the way a W1-A component resulting from a blood vessel internal volume change below a cuff central portion A forms and changes in the cuff depressurizing process.

FIG. 5 is an exemplary view that depicts the way the W1-A component resulting from the blood vessel internal volume change below the cuff central portion A forms and changes in the cuff depressurizing process.

In graph 1, the abscissa represents the elapsed time when the cuff pressure is reduced at a constant depressurization rate, the ordinate represents the blood vessel internal/external pressure difference (blood vessel internal pressure−cuff pressure), and the invasive waveform (blood vessel internal pressure change) is simplified by a triangular waveform. Based on these conditions, graph 1 represents the change (the same triangular waveform as the invasive waveform) in blood vessel internal/external pressure difference below the cuff central portion A, which results from the invasive waveform (blood vessel internal pressure change) at each point of the elapsed time.

Above graph 1, graph 2 represents the change in blood vessel internal volume at each point of time, which occurs in response to the change in blood vessel internal/external pressure difference, by plotting the blood vessel internal volume on the ordinate. On the left side of the ordinate of the blood vessel internal/external pressure difference, graph 3 represents a blood vessel internal/external pressure difference-blood vessel internal volume relationship that converts the blood vessel internal/external pressure difference change (graph 1) into the blood vessel internal volume change (graph 2), by plotting the blood vessel internal volume on the abscissa.

As the blood vessel internal/external pressure difference-blood vessel internal volume relationship of graph 3, a simplified relationship is assumed by noting the tendency that the blood vessel internal volume abruptly changes (abruptly increases or decreases) near the position where the blood vessel internal/external pressure difference is 0. That is, a line including two bent portions at points where the blood vessel internal volume is V0 and V1, a steep gradient portion between V0 and V1, and gentle gradient portions smaller than V0 and larger than V1 represents the change between the state (the blood vessel internal volume is 0) in which the blood vessel is completely closed and the state (the blood vessel internal volume is Vmax) in which the blood vessel is completely open in the process during which the blood vessel internal/external pressure difference increases and decreases.

This indicates two tendencies: one is the tendency that the blood vessel is collapsed by its own weight (the blood vessel internal volume is V0) in a position where the blood vessel internal/external pressure difference is 0, but, when the blood vessel internal/external pressure difference changes from this position to a positive value, the blood vessel internal volume abruptly increases to reach the state in which the blood vessel is sufficiently open (the blood vessel internal volume is V1), and the blood vessel internal volume gradually increases (toward the maximum blood vessel internal volume Vmax) with respect to the change in blood vessel internal/external pressure difference after that; and the other is the tendency that when the blood vessel internal/external pressure difference changes from the position where it is 0 to a negative value, the blood vessel internal volume gradually decreases (toward a blood vessel internal volume of 0). Note that in graph 3, the steep gradient portion between the positions where the blood vessel internal volume is V0 and V1 is approximated by a straight line, so the ratio of the change in blood vessel internal volume remains the same in this portion. In practice, however, the ratio of the change is maximum at the position where the blood vessel internal/external pressure difference is 0 (the position where the blood vessel internal volume is V0).

The degree of the tendency that the blood vessel internal volume abruptly changes (abruptly increases) near the position where the blood vessel internal/external pressure difference is 0 depends on the extensibility of the blood vessel of a person to be measured. However, the tendency itself is presumably generalizable.

In the cuff depressurizing process (elapsed time) of graph 1, a, b, and c indicate the change (triangular wave) in blood vessel internal/external pressure difference below the cuff central portion A, when the cuff pressure is equal to the systolic blood pressure value, when the cuff pressure is in almost the middle of the systolic blood pressure value and diastolic blood pressure value, and when the cuff pressure is equal to the diastolic blood pressure, respectively.

The changes (triangular waveforms) a, b, and c in blood vessel internal/external pressure difference at the individual points of the elapsed time each have an apex (peak point) resulting from the portion of the systolic blood pressure value (that is, the initial diastolic period of the heart) in the invasive waveform (blood vessel internal pressure change), and a downward apex (bottom point) resulting from the portion of the diastolic blood pressure value (that is, the initial systolic period of the heart) in the invasive waveform (blood vessel internal pressure change).

(a), (b), and (c) in graph 2 respectively indicate the results when the changes in blood vessel internal/external pressure difference of a, b, and c in graph 1 are converted into the changes in blood vessel internal volume by using the blood vessel internal/external pressure difference-blood vessel internal volume relationship in graph 3. In (a), (b), and (c), hollow circles indicate the positions (two, front and back portions) of the initial systolic period of the heart. Each hollow circle corresponds to the downward apex (bottom point) of the invasive waveform (blood vessel internal pressure change). A component (indicated by the thick line) shown between the positions (two, front and back portions) of the initial systolic period of the heart is the W1-A component. That is, graph 2 shows the way the W1-A component changes at each point of time in the cuff depressurizing process (elapsed time).

In the W1-A components (blood vessel internal volume changes) of (b) and (c), each dot indicates the position where the blood vessel internal/external pressure difference is 0 before the peak point. In the W1-A component (blood vessel internal volume change) of (a), the peak point corresponds to the position where the blood vessel internal/external pressure difference is 0, and a dot indicates this position. The position where the blood vessel internal/external pressure difference is 0, which is indicated by the dot in each of (a), (b), and (c), is actually a portion (a maximum gradient point in the first half of the waveform) where the blood vessel internal volume abruptly increases (abruptly rises).

In addition, in the W1-A components of (a), (b), and (c), a position where the blood vessel internal volume is minimum, which comes after the peak point, is also indicated by a dot. This position where the blood vessel internal volume is minimum, which comes after the peak point of the W1-A component, is almost equal to the position of the downward peak point (bottom point) of an actual pulse wave signal. Accordingly, the position where the blood vessel internal volume is minimum, which comes after the peak point of the W1-A component, will be called a bottom point of the W1-A component.

In graph 2, t1 indicates a time (time difference) by which the portion (the maximum gradient point in the first half of the waveform) where the blood vessel internal volume abruptly rises in the W1-A component [the position indicated by the dot where the blood vessel internal/external pressure difference is 0] lags behind the position of the initial systolic period leading the W1-A component, and T indicates one period of the pulse wave signal. The period T of the pulse wave signal is practically constant during the measurement period. Also, H indicates the displacement of the bottom point of the W1-A component below the portion (the maximum gradient point in the first half of the waveform) where the blood vessel internal volume abruptly rises.

As indicated by (a), (b), and (c) in graph 2, the time difference t1 decreases as the cuff pressure approaches the diastolic blood pressure value from the systolic blood pressure value. That is, the time difference t1 between the preceding bottom point and the appearance of the maximum gradient point decreases as the cuff pressure approaches the diastolic blood pressure value from the systolic blood pressure value.

Since the period T of the pulse wave signal is practically constant during the measurement period, a phase difference $2\pi$ (t1/T) between the preceding bottom point and the appearance of the maximum gradient point similarly decreases as the cuff pressure approaches the diastolic blood pressure value from the systolic blood pressure value.

As indicated by (c) in graph 2, when the cuff pressure is equal to the diastolic blood pressure value, the preceding bottom point and maximum gradient point (abrupt rising point) of the W1-A component and the initial systolic period occur at the same time, that is, t1=0, in this simplified graph.

Features of Pulse Wave Signal

The contents of the simplified examination of the W1-A component obtained by dividing the pulse wave signal PW into components have been described above. In practice, however, the pulse wave signal PW is not separated into the W1-A and W0 components but detected as one pulse wave signal, on which the W1-A and W0 components are superposed, by the small cuff 2 for detecting a pulse wave.

As described previously, however, although the W0 component is reflected on the leading edge, the W1-A component largely reflects the shape of the W1 component of the pulse wave signal to be superposed on the cuff pressure. In addition, the W2 component of the pulse wave signal is generally smaller than the W1 component, and disappears when the cuff pressure is close to the diastolic blood pressure value.

Accordingly, if the pressure change (W0 component) due to pressure propagation and the pressure change (W1 component) due to the blood vessel internal volume change are superposed as they are temporarily shifted, the slope from the bottom to the peak of the pulse wave largely changes and produces a notch.

Determination of Blood Pressure Values

Accordingly, the blood pressure values can be determined as follows based on the above-described features of the pulse wave signal.

Systolic Blood Pressure Value:

When the cuff pressure is higher than the systolic blood pressure value, the W1-A and W1-C components do not exist, so a signal of the W0 component is obtained. When the cuff pressure becomes equal to the systolic blood pressure value, the W1-A and W1-C components appear, and a notch is produced. Therefore, when detecting a pulse wave (a pulse wave containing the produced notch) in which the W1-A and W1-C components are superposed on the pressure propagation component, the systolic blood pressure value is obtained from the corresponding cuff pressure.

Accordingly, the systolic blood pressure value can accurately be derived by the following method.

Procedure 1. For each one-period pulse wave, a tangent of the pulse wave is derived at a maximum change point indicating a maximum slope between the vicinity of the pulse wave base and the maximum pulse wave amplitude point of the pulse wave.

Procedure 2. For each one-period pulse wave, a difference H between the value of the intersection of the tangent derived at the time of the pulse wave base by procedure 1 and a pulse wave level actually measured at the time of the pulse wave base is obtained.

Procedure 3. A cuff pressure at a point of time at which the different H derived for each one-period pulse wave abruptly departs from the vicinity of 0 (a point of time at which the difference H abruptly increases in the measurement during the depressurizing process) is determined as the systolic blood pressure value.

Figure 6A:
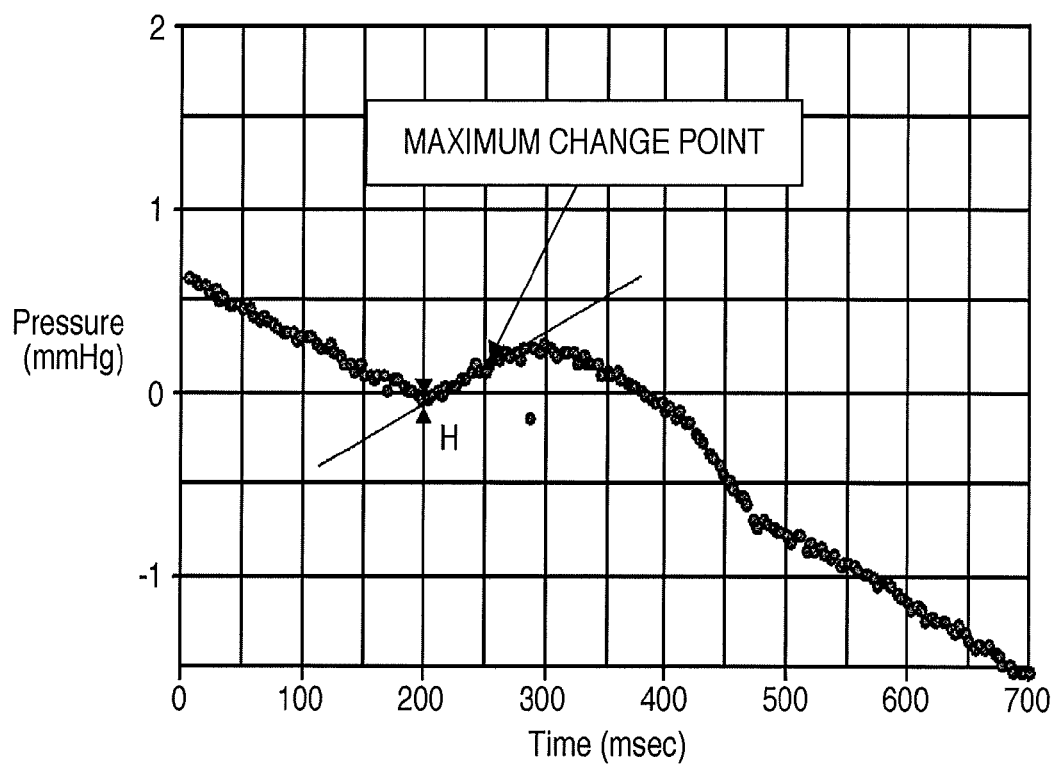
FIG. 6A is an exemplary view for explaining a systolic blood pressure value deriving method.
Figure 6B:
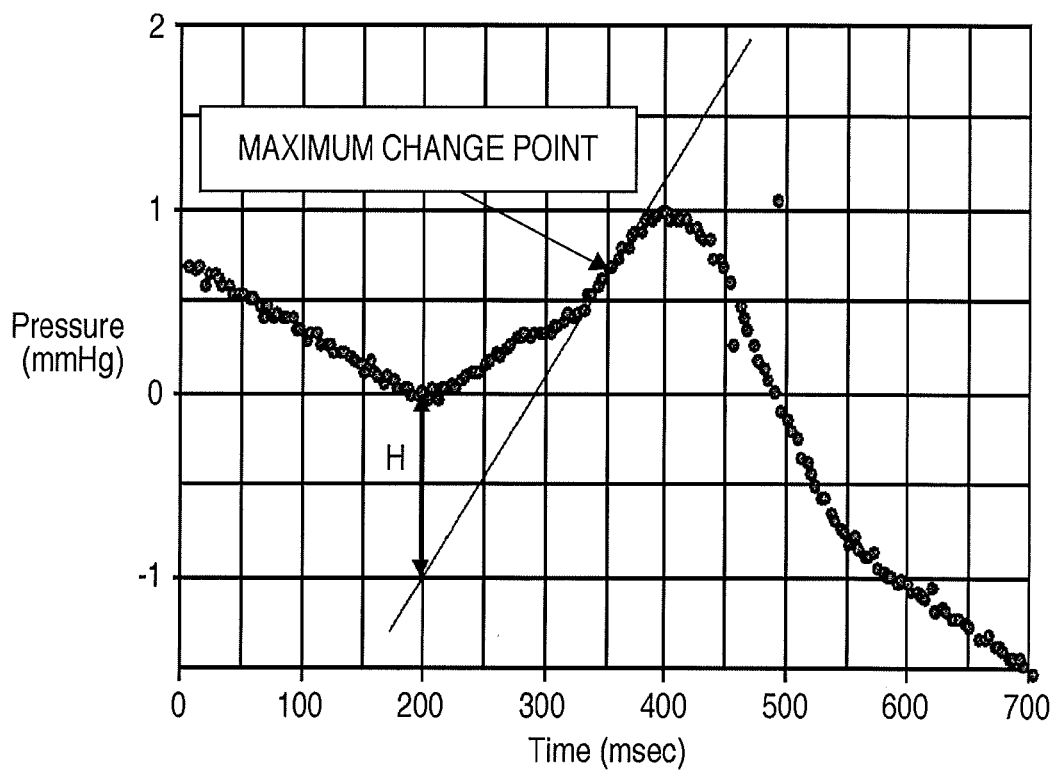
FIG. 6B is an exemplary view for explaining the systolic blood pressure value deriving method.

FIGS. 6A and 6B are exemplary views for explaining the systolic blood pressure value deriving method. FIG. 6A shows an example in which the cuff pressure is higher than the systolic blood pressure value. FIG. 6B shows an example in which the cuff pressure is equal to or lower than the systolic blood pressure value.

As shown in FIGS. 6A and 6B, since a notch is produced at the point of the systolic blood pressure value, the maximum change point departs from the pulse wave base, and the difference H rapidly dramatically increases. This demonstrates that the cuff pressure at the point of time at which the difference H abruptly changes can be used as the systolic blood pressure value. Note that the same processing can be performed even when obtaining, instead of H, the area between the tangent and pulse wave from the vicinity of the pulse wave base to the maximum change point, and using the change in this value.

Diastolic Blood Pressure Value:

As the cuff pressure approaches the diastolic blood pressure value, a time difference T between the time of the leading edge of the pulse wave (the lowest point of the pulse pressure) and the time of the maximum change point (notch) of the slope decreases, and the component (W0 component) due to pressure propagation cannot be separated from W1-A and W1-C any longer. Accordingly, this point at which separation is no longer possible need only be detected.

It is, therefore, possible to accurately derive the diastolic blood pressure value by the following method.

Procedure 1. For each one-period pulse wave, a tangent of the pulse wave is derived at a maximum change point indicating a maximum slope between the vicinity of the pulse wave base and the maximum pulse wave amplitude point of the pulse wave.

Procedure 2. For each one-period pulse wave, a difference H between the value of the intersection of the tangent derived at the time of the pulse wave base by procedure 1 and a pulse wave level actually measured at the time of the pulse wave base is obtained.

Procedure 3. A cuff pressure at a point of time at which the different H derived for each one-period pulse wave abruptly approaches a predetermined value close to 0 (a point of time at which the difference H abruptly decreases in the measurement during the depressurizing process) is determined as the diastolic blood pressure value.

Figure 7A:
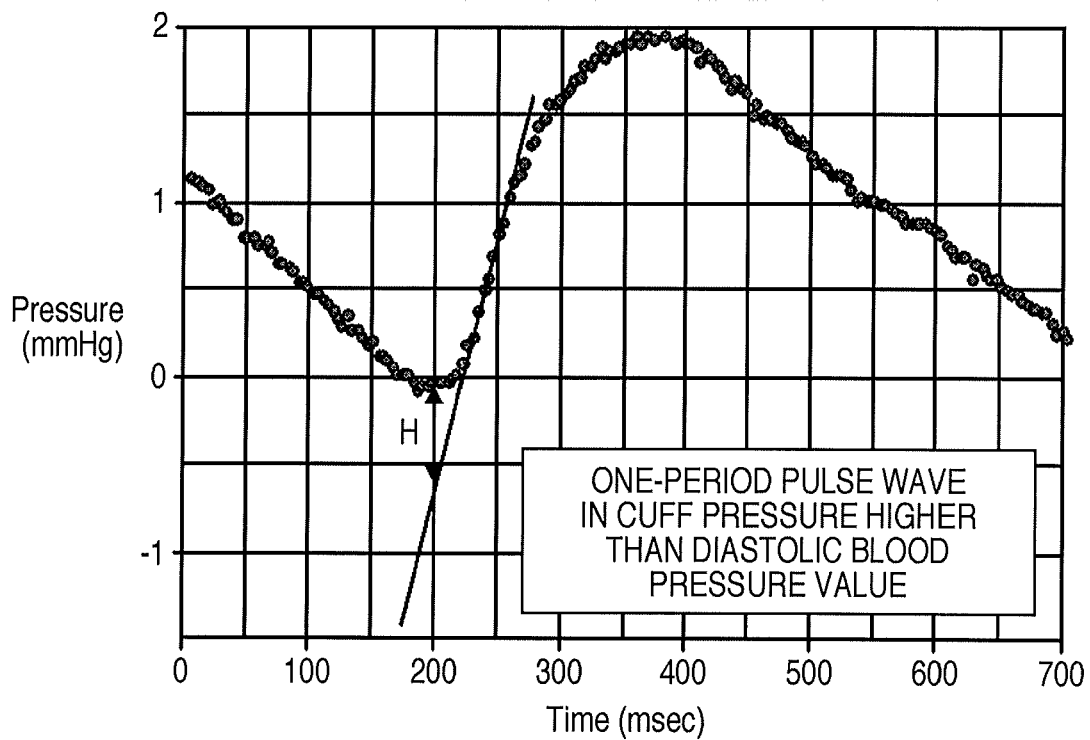
FIG. 7A is an exemplary view for explaining a diastolic blood pressure value deriving method.
Figure 7B:
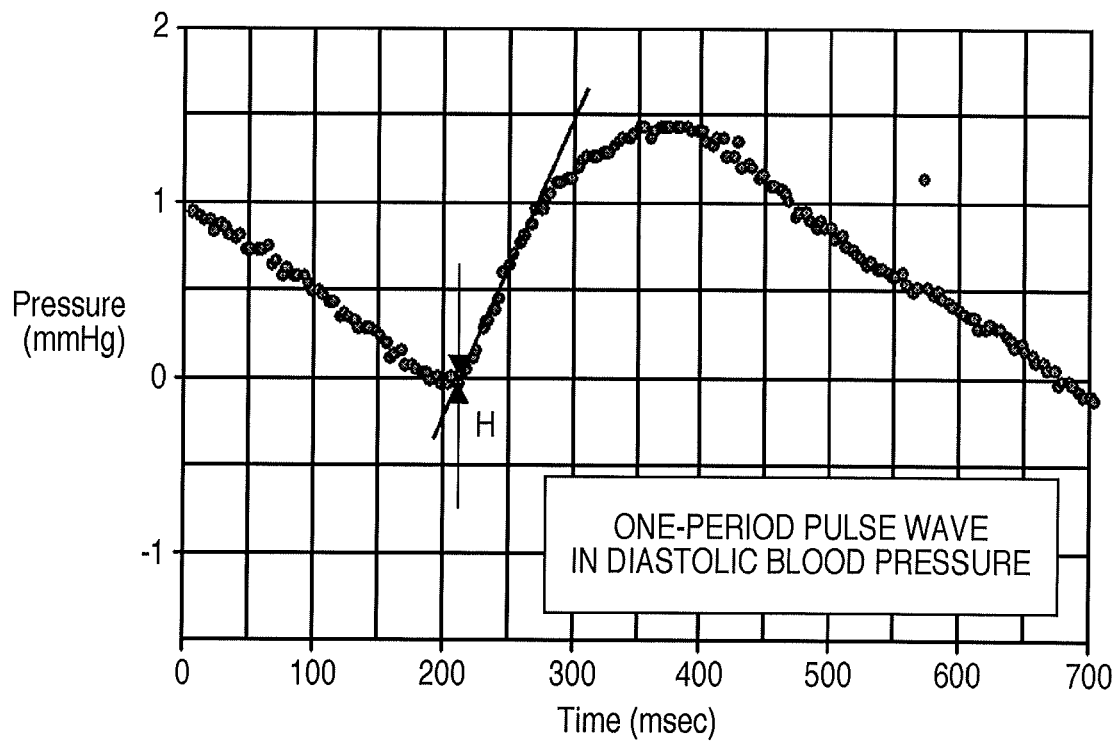
FIG. 7B is an exemplary view for explaining the diastolic blood pressure value deriving method.

FIGS. 7A and 7B are exemplary views for explaining the diastolic blood pressure value deriving method. FIG. 7A shows an example in which the cuff pressure is higher than the diastolic blood pressure value. FIG. 7B shows an example in which the cuff pressure is equal to or lower than the diastolic blood pressure value.

As shown in FIGS. 7A and 7B, at the point of the diastolic blood pressure value, the difference H rapidly dramatically increases because the maximum change point approaches the pulse wave base. This indicates that the cuff pressure at the point of time at which the difference H abruptly changes can be used as the diastolic blood pressure value. Note that the same processing can be performed even when obtaining, instead of H, the area between the tangent and pulse wave from the vicinity of the pulse wave base to the maximum change point, and using the change in this value.

Note that the comparison of the procedures of deriving the systolic blood pressure value and diastolic blood pressure value described above shows that the procedures (algorithms) are almost the same.

Figure 8:
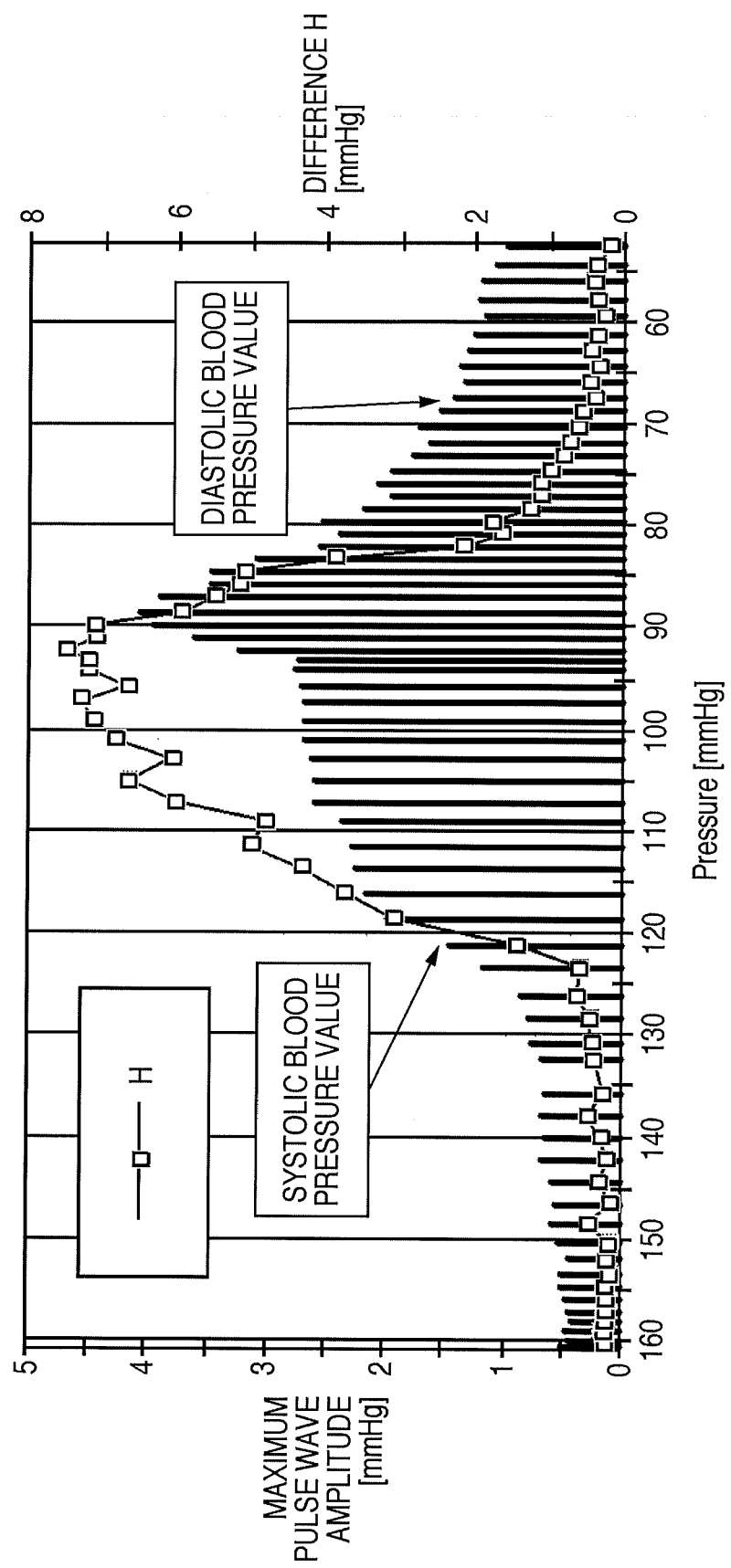
FIG. 8 is an exemplary view that depicts time-series changes in maximum pulse wave amplitude and difference H measured in the depressurizing process.

FIG. 8 is an exemplary view that depicts time-series changes in maximum pulse wave amplitude and difference H in the measurement during the depressurizing process. FIG. 8 shows that an abrupt change point of the time-series change in difference H well corresponds to the systolic blood pressure value and diastolic blood pressure value.

As described above, the bottom point and maximum gradient point (abrupt rising point) of the pulse wave signal are detected in each individual pulse wave signal. Also, the predetermined threshold values are set by taking account of, for example, noise during the course of processing the detected pulse wave signal. Note that the effects of individual differences and the measurement conditions such as the depressurization rate on, for example, noise in the course of the signal processing are generally small.

Unlike the conventional oscillometric sphygmomanometer, these blood pressure value determination methods need not process the change profile of a pulse wave amplitude value in the cuff depressurizing process using parameters (for example, the ratio of the pulse wave amplitude value to the maximum pulse wave amplitude value, which is set based on a statistical method) on which the individual differences of a person to be measured and the measurement conditions (for example, the depressurization rate) have large effects. This makes it possible to perform measurement by reducing variations caused by individual differences and the measurement conditions (for example, the depressurization rate).

Operation of Apparatus

Figure 9:
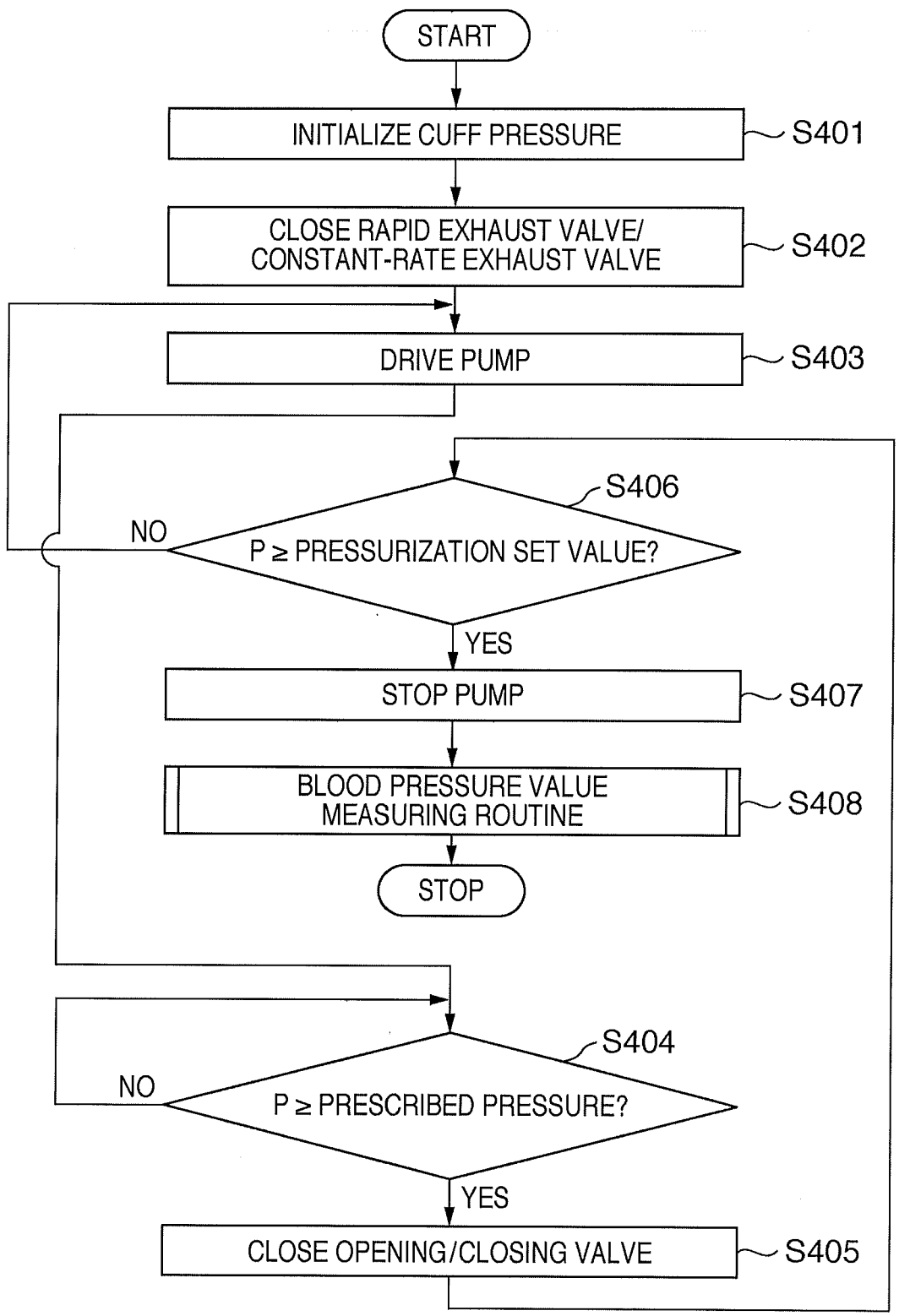
FIG. 9 is a flowchart that depicts the operation of a cuff pressurizing routine of the blood pressure measuring apparatus according to the first embodiment.

FIG. 9 is a flowchart that depicts the operation of the cuff pressurizing routine.

First, the cuff main body 201 is attached to the upper arm. When the measurement start switch 242 (not shown) is pressed after that, the air bladders are deflated by fully opening the opening area of the rapid exhaust valve/constant-rate exhaust valve 222, and opening the opening/closing valve 216. When the residual air in each air bladder is completely exhausted, zero setting (initialization) of the pressure sensor 231 is performed in step S401.

In step S402, the rapid exhaust valve/constant-rate exhaust valve 222 is completely closed while the opening/closing valve 216 is kept open. This makes the cuff (the compression air bladder, pulse wave detection air bladder, and sub air bladder) ready for pressurization. In step S403, electric power is supplied to the pump 223.

Subsequently, in step S404, whether a prescribed pressure (a pressure that does not interfere with blood flow occlusion and inflates the sub air bladder 207 so as to reduce the cuff-edge effect) is reached is checked. If the prescribed pressure is reached, the opening/closing valve 216 is closed in step S405.

In step S406, whether the cuff pressure is equal to or higher than a pressurization set value is determined. If the cuff pressure is equal to or higher than the pressurization set value, the process advances to step S407 to stop the pump driving and start a blood pressure value measuring routine. Thus, the pump 223 is continuously driven to set the pressure of the compression air bladder 408 at a pressurization set value higher than a predicted systolic blood pressure by 20 to 30 mmHg.

Figure 10:
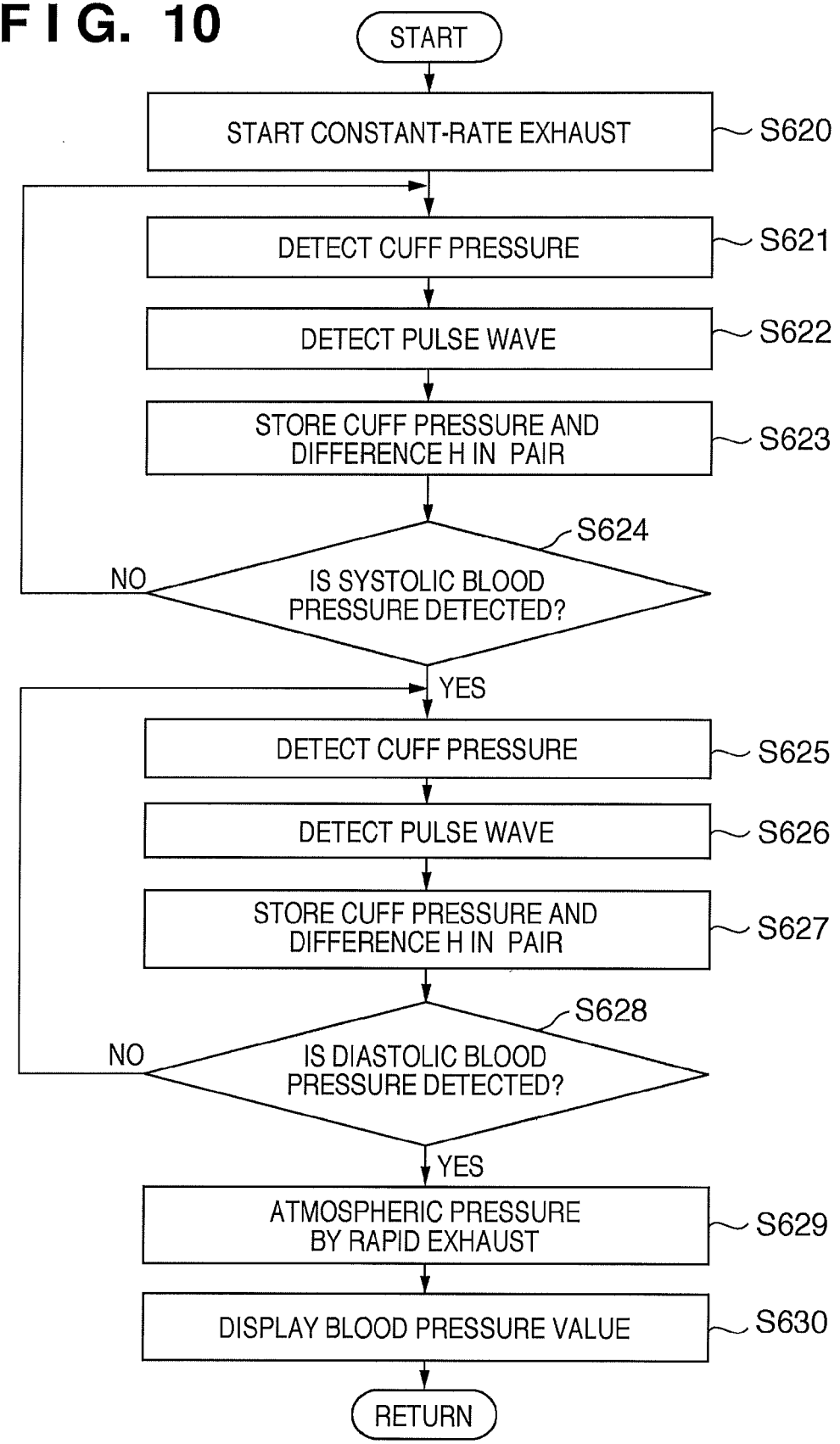
FIG. 10 is a detailed flowchart of a blood pressure value measuring routine.

FIG. 10 is a flowchart that depicts the blood pressure value measuring routine. Note that this routine uses the above-described difference H in the determination of the blood pressure.

When the process advances to step S620, the rapid exhaust valve/constant-rate exhaust valve 222 starts constant-rate exhaustion. That is, the cuff pressure controller 240 starts constant-rate depressurization by changing the opening area of the rapid exhaust valve/constant-rate exhaust valve 222 such that the depressurization rate is 2 to 3 mmHg/sec, by using a signal from the cuff pressure detection unit.

Subsequently, in step S621, the cuff pressure is obtained from the cuff pressure detection unit. In step S622, a pulse wave signal is detected, a maximum change point (notch) of each pulse wave signal is detected, and a tangent at the maximum change point is derived. Then, the difference H between the value of the intersection of the tangent at the time of the pulse wave base and a pulse wave level actually measured at the time of the pulse wave base is calculated. After that, the process advances to step S623 to store the difference H derived by the pulse wave processor 239 and the cuff pressure as a pair in the RAM 238.

In step S624, whether the difference H stored in step S623 has largely fluctuated from the vicinity of 0 is determined, and a cuff pressure value at the point of time of this fluctuation is determined as the systolic blood pressure value. Note that it is also possible to predetermine a threshold value, and determine, as the systolic blood pressure value, a cuff pressure value when the difference H has exceeded the threshold value. If there is no fluctuation, the process returns to step S621.

In step S626, a pulse wave signal is detected again after the systolic blood pressure value is determined, a maximum change point (notch) of each pulse wave signal is detected, and a tangent at the maximum change point is derived. Then, the difference H between the value of the intersection of the tangent at the time of the pulse wave base and a pulse wave level actually measured at the time of the pulse wave base is calculated. After that, the process advances to step S627 to store the difference H derived by the pulse wave processor 239 and the cuff pressure as a pair in the RAM 238.

In step S628, whether the difference H stored in step S626 has approached a predetermined value close to 0 is determined, and a cuff pressure value at the point of time of this approach is determined as the diastolic blood pressure value. Note that it is also possible to predetermine a threshold value, and determine, as the diastolic blood pressure value, a cuff pressure value when the difference H has become smaller than the threshold value. If the difference H has not become smaller than the threshold value, the process returns to step S625.

In step S629, the cuff is set at the atmospheric pressure by fully opening the opening area of the rapid exhaust valve/constant-rate exhaust valve 222 and opening/closing valve 216.

In step S630, the display unit displays the stored systolic blood pressure value and diastolic blood pressure value, thereby terminating the series of the blood pressure measuring operations.

As has been explained above, the blood pressure measuring apparatus according to the first embodiment determines the blood pressure values (systolic blood pressure value and diastolic blood pressure value) based on the change in shape of a pulse wave signal (one-period pulse wave signal) without using any statistical method. Consequently, it is possible to perform measurement suited to individual differences, and derive high-accuracy blood pressure values (systolic blood pressure value and diastolic blood pressure value).

As explained above with reference to FIG. 8, the difference H changes with a favorable correspondence near the systolic blood pressure value and diastolic blood pressure value. This makes high-accuracy detection feasible. Also, blood pressure values corresponding to the systolic blood pressure value and diastolic blood pressure value are detected by the same simple calculation algorithm. Accordingly, the present invention has the advantage that the blood pressure values can be detected with less calculation resources.

The present invention is not limited to the above embodiment and various changes and modifications can be made without departing from the spirit and scope of the invention. Therefore, to apprise the public of the scope of the present invention, the following claims are appended.

The invention claimed is:
1. A blood pressure measuring apparatus comprising:
a cuff member comprising a compression air bladder which is adapted to be formed on a side to be brought into contact with a blood pressure measurement portion and which is adapted to press a whole blood pressure measurement portion, a sub air bladder which is adapted to be formed on a side of said compression air bladder, which is brought into contact with the blood pressure measurement portion, and which is adapted to press a heart side of a blood vessel in the blood pressure measurement portion, and a pulse wave detection air bladder which is adapted to be formed on the side of said compression air bladder, which is brought into contact with the blood pressure measurement portion, and which is adapted to detect a pulse wave on a slightly downstream side of a central portion of the blood vessel in the blood pressure measurement portion;
pressure control means for pressurizing or depressurizing each air bladder of said cuff member;
a pressure sensor which senses an internal pressure of each air bladder of said cuff member;

pulse wave signal extracting means for extracting time-series data of a pulse wave signal superposed on a cuff internal pressure sensed by said pressure sensor, in the process during which said pressure control means pressurizes or depressurizes each air bladder of said cuff member; and blood pressure value deriving means for deriving a systolic blood pressure value and/or a diastolic blood pressure value based on a change in feature amount of the pulse wave signal and a cuff internal pressure at a point of time of the change, wherein said blood pressure value deriving means detects, for each of a plurality of one-period pulse wave signals contained in the pulse wave signal time-series data, a maximum gradient point of the one-period pulse wave in a period between a peak point and a bottom point appearing prior to the peak point, and derives the systolic blood pressure value and/or the diastolic blood pressure value based on a difference between a pulse wave amplitude value at a bottom point appearing prior to the detected maximum gradient point and a value, which is obtained at a time of the bottom point, of a tangent passing through the detected maximum gradient point.

2. A blood pressure measuring apparatus comprising:

a cuff member comprising a compression air bladder which is adapted to be formed on a side to be brought into contact with a blood pressure measurement portion and which is adapted to press a whole blood pressure measurement portion, a sub air bladder which is adapted to be formed on a side of said compression air bladder, which is brought into contact with the blood pressure measurement portion, and which is adapted to press a heart side of a blood vessel in the blood pressure measurement portion, and a pulse wave detection air bladder which is adapted to be formed on the side of said compression air bladder, which is brought into contact with the blood pressure measurement portion, and which is adapted to detect a pulse wave on a slightly downstream side of a central portion of the blood vessel in the blood pressure measurement portion;

pressure control means for pressurizing or depressurizing each air bladder of said cuff member;

a pressure sensor which senses an internal pressure of each air bladder of said cuff member;

pulse wave signal extracting means for extracting time-series data of a pulse wave signal superposed on a cuff internal pressure sensed by said pressure sensor, in the process during which said pressure control means pressurizes or depressurizes each air bladder of said cuff member; and blood pressure value deriving means for deriving a systolic blood pressure value and/or a diastolic blood pressure value based on a change in feature amount of the pulse wave signal and a cuff internal pressure at a point of time of the change, wherein said blood pressure value deriving means detects, for each of a plurality of one-period pulse wave signals contained in the pulse wave signal time-series data, a maximum gradient point of the one-period pulse wave in a period between a peak point and a bottom point appearing prior to the peak point, and derives the systolic blood pressure value and/or the diastolic blood pressure value based on an area of a portion bounded by a tangent passing through the detected maximum gradient point and the pulse wave signal in a period between the maximum gradient point and a bottom point appearing prior to the maximum gradient point.

3. A method of controlling a blood pressure measuring apparatus comprising a cuff member comprising a compression air bladder which is adapted to be formed on a side to be brought into contact with a blood pressure measurement portion and which is adapted to press a whole blood pressure measurement portion, a sub air bladder which is adapted to be formed on a side of the compression air bladder, which is brought into contact with the blood pressure measurement portion, and which is adapted to press a heart side of a blood vessel in the blood pressure measurement portion, and a pulse wave detection air bladder which is adapted to be formed on the side of the compression air bladder, which is brought into contact with the blood pressure measurement portion, and which is adapted to detect a pulse wave on a slightly downstream side of a central portion of the blood vessel in the blood pressure measurement portion, pressure control means for pressurizing or depressurizing each air bladder of the cuff member, and a pressure sensor which senses an internal pressure of each air bladder of the cuff member, said method comprising:

a pulse wave signal extracting step performed by a processor to extract time-series data of a pulse wave signal superposed on a cuff internal pressure sensed by the pressure sensor, in the process during which the pressure control means pressurizes or depressurizes each air bladder of the cuff member; and a blood pressure value deriving step performed by the processor to derive a systolic blood pressure value and/or a diastolic blood pressure value based on a change in feature amount of the pulse wave signal and a cuff internal pressure at a point of time of the change, wherein in the blood pressure value deriving step, for each of a plurality of one-period pulse wave signals contained in the pulse wave signal time-series data, a maximum gradient point of the one-period pulse wave is detected in a period between a peak point and a bottom point appearing prior to the peak point, and the systolic blood pressure value and/or the diastolic blood pressure value is derived based on a difference between a pulse wave amplitude value at a bottom point appearing prior to the detected maximum gradient point and a value, which is obtained at a time of the bottom point, of a tangent passing through the detected maximum gradient point.

4. A method of controlling a blood pressure measuring apparatus comprising a cuff member comprising a compression air bladder which is adapted to be formed on a side to be brought into contact with a blood pressure measurement portion and which is adapted to press a whole blood pressure measurement portion, a sub air bladder which is adapted to be formed on a side of the compression air bladder, which is brought into contact with the blood pressure measurement portion, and which adapted to press a heart side of a blood vessel in the blood pressure measurement portion, and a pulse wave detection air bladder which is adapted to be formed on the side of the compression air bladder, which is brought into contact with the blood pressure measurement portion, and which is adapted to detect a pulse wave on a slightly downstream side of a central portion of the blood vessel in the blood pressure measurement portion, pressure control means for pressurizing or depressurizing each air bladder of the cuff member, and a pressure sensor which senses an internal pressure of each air bladder of the cuff member, said method comprising:

a pulse wave signal extracting step performed by a processor to extract time-series data of a pulse wave signal superposed on a cuff internal pressure sensed by the pressure sensor, in the process during which the pressure control means pressurizes or depressurizes each air bladder of the cuff member, and a blood pressure value deriving step performed by the processor to derive a systolic blood pressure value and/or a diastolic blood pressure value based on a change in feature amount of the pulse wave signal and a cuff internal pressure at a point of time of the change, wherein in the blood pressure value deriving step, for each of a plurality of one-period pulse wave signals contained in the pulse wave signal time-series data, a maximum gradient point of the one-period pulse wave is detected in a period between a peak point and a bottom point appearing prior to the peak point, and the systolic blood pressure value and/or the diastolic blood pressure value is derived based on an area of a portion bounded by a tangent passing through the detected maximum gradient point and the pulse wave signal in a period between the maximum gradient point and a bottom point appearing prior to the maximum gradient point.

* * * * *